United States Patent [19]
Maekawa et al.

[11] Patent Number: 4,948,413
[45] Date of Patent: Aug. 14, 1990

[54] PHYSIOLOGICALLY ACTIVE AGENT FOR AGRICULTURE USE

[75] Inventors: Yoshio Maekawa, Miki; Osamu Yagyu, Kakogawa; Hironori Mizuno, Kakogawa; Minoru Okumura, Kakogawa; Shigeru Isoda, Kakogawa; Kaoru Yagi, Himeji, all of Japan

[73] Assignee: Taki Chemical Co., Ltd., Kakogawa, Japan

[21] Appl. No.: 195,731

[22] Filed: May 16, 1988

[30] Foreign Application Priority Data

Jun. 4, 1987 [JP] Japan .................................. 62-141149
Dec. 8, 1987 [JP] Japan .................................. 62-311634

[51] Int. Cl.$^5$ ...................... A01N 3/02; A01N 59/00; A01N 11/08
[52] U.S. Cl. .......................................... 71/65; 71/77; 71/79; 71/94; 71/7; 71/11; 424/93; 514/345

[58] Field of Search ..................... 71/7, 11, 65, 77, 79, 71/94; 514/345; 424/93

[56] References Cited

FOREIGN PATENT DOCUMENTS 0203708 12/1986 European Pat. Off. .
1229801 10/1986 Japan .
1246105 11/1986 Japan .

OTHER PUBLICATIONS

Chem. Abst. 66:64540W, 1967.
Chem. Absts. 81:60639X-:60642t, 1974.

Primary Examiner—John W. Rollins
Attorney, Agent, or Firm—Armstrong, Nikaido, Marmelstein, Kubovcik & Murray

[57] ABSTRACT

A mixture of 2-piperidone and an N-acyllactam compound for use as a soil amending agent which is provided in a molar ratio of 2-piperidone to N-acyllactam compound in the range from 0.1:1 to 10:1 is effective in the promotion of plant growth.

3 Claims, No Drawings

PHYSIOLOGICALLY ACTIVE AGENT FOR AGRICULTURE USE

The present invention relates to a physiologically active agent for agricultural use.

A primary object of the present invention is to provide a physiologically active agent or said amending agent for agricultural use which is high in the effect of stimulating or promoting the growth of plant roots.

A further object of the present invention is to provide a physiologically active agent for agricultural use which is high in the effect of promoting the growth of leguminous bacteria of the genus Rhizobium and actinomycetes of the genus Streptomyces in soil.

Another object of the present invention is to provide a physiologically active agent for agricultural use which is high in the effect of controlling the domination in soil of pathogenic fungi imperfecti and bacteria of the genus Pseudomonas which are responsible for plant diseases.

Still another and most important object of the present invention is to provide a physiologically active agent for agricultural use which promotes the growth of plant roots, helps balance the microbial flora in soil, and assures normal soil environment over long periods.

In order to ensure a high yield of agricultural products, it is necessary that the growing plants actively take in essential nutrients and maintain themselves in a healthy condition till the end of harvesting. What is all-important to this end is to keep the soil environment in optimum conditions.

The recent development of controlled agriculture has resulted in the use of various agricultural chemicals and inorganic fertilizers in large quantities.

The excessive use of agricultural chemicals has caused chemical injuries to crops, and also disturbed microbial flora in soil, thus entailing new problems such as diversified plant disease injuries and simultaneous occurence of several types of diseases.

The use of inorganic fertilizers in large quantities, on the other hand, has promoted mineralization of soil, leading to a reduction in crop yield due to the lowered field resistance and fertility, frequent occurence of disease injuries caused by reduction in the number of microorganisms in soil, and other problems.

In addition, the use of agricultural chemicals has been an issue of major social concern because of the environmental pollution caused by residual chemicals to soil and plants and of chemical injuries to environmental animals including humans.

In order to avoid these problems, thereby ensuring normal growth of plants and high yield of agricultural products, consideration must be given to the whole growth environment for plants, especially their roots and the related group of livings.

Now that the mechanism of biological interactions in rhizosphere environment of soil is clear, importance has been put on the interaction between growing plants and the group of livings closely related thereto.

A normal rhizosphere environment means a wide rhizosphere in which many microorganisms are found in both number and kind. What are required for the creation of such a rhizosphere are that the growth of plant roots therein is normal, and that, in the surrounding microbial flora, microorganisms useful for the growth of plant roots (for example, actinomycetes and leguminous bacteria of the genus Rhizobium) are found in relatively larger quantities, while those which directly participate in the occurence of disease injuries (for example, bacteria of the genus Pseudomonas and pathogenic fungi imperfecti of Fusarium and other gen.) are present in relatively smaller quantities. Such a well-balanced rhizosphere condition brings about a high yield of agricultural products and prevents the occurence of disease injuries.

Thus, the important requirements are (1) promoting the growth of roots (plants), (2) proliferating leguminous bacteria of the genus Rhizobium and actinomycetes of the genus Streptomyces which are useful for growing plants (soil), and (3) suppressing the domination of bacteria of the genus Pseudomonas and pathogenic fungi imperfecti which are responsible for the occurence of disease injuries.

Problems associated with each of the above three requirements are detailed below.

(1) Promotion of the growth of plant roots

Auxins, gibberellins, cytokinins and brassinolides are known as plant growth regulators. These compounds, however, have the following problems: (i) high cost, (ii) difficulty in manufacturing, and (iii) marked difference in efficacy depending on the time of application and the type of plant.

(2) Proliferation of useful microorganisms

It is known that leguminous bacteria of the genus Rhizobium (hereinafter abbreviated as leguminous bacteria) infect the roots of legumes to form nodules (symbiosis), thus supplying auxins and nitrogen sources, and that the larger the number and size of nodules formed, the higher the crop yield.

It is generally considered that the symbiosis between the leguminous bacteria and legumes is based on a certain discrimination mechanism existing between the bacteria and the root-hair cells. For example, "Molecular Biology of the Cell" (written by Bruce Alberts, et al., and published from Kyoiku-sha, Nov. 15, 1985) suggests that the root hairs of a legume recognize a certain saccharide on the cell wall surface of leguminous bacteria, thereby inducing a specific bonding between them and establishing symbiosis. The book also describes that the leguminous bacteria, once put in symbiosis with the root hairs, lose most of their cell walls and take a gigantic, branched and club-like shape called bacteroid.

Based on these findings, it has been a common practice to distribute luguminous bacteria in soil at the time of fertilizer or growth regulator application for a higher yield of crops. Actually, however, the increase in the number of leguminous bacteria in soil does not always lead to the increase in the number of bacteria in the plant roots, with little of the intended effect being achieved. Actinomycetes of the genus Streptomyces include about 800 species (the largest number of all actinomycetes), and occupy more than 90% of the total actinomycetes in soil. Microorganisms of this group are known to play an important role in the mechanism of controlling plant diseases in soil. Various attempts have been made to utilize these useful microorganisms (for example, direct application to soil), but no appreciable effect has yet been achieved because of the low rate of colonization in soil.

Under the circumstances, a substance that promotes effective colonization of actinomycetes of the genus Streptomyces, if available, would be of great value in minimizing disease injuries in agriculture.

(3) Controlling harmful bacteria

Pathogenic fungi imperfectii and strains of the genus Pseudomonas dominate the microbial flora in soil when plant disease injuries occur, indicating that these bacteria are primarily responsible for these hazards.

Various agricultural chemicals have been applied to control these bacteria and breeding of disease-resistant varieties have been tried to minimize such hazards, but no appreciable effect has yet been achieved.

As described above, the crop growth environment involves a variety of important factors. Intensive studies on physiologically active substances for agricultural use with consideration given to all these points have led us to discover that the above-mentioned problems can be solved by the use of a physiologically active agent comprising a specific N-acyl lactam compound and 2-piperidone, which is very effective in promoting the growth of plant roots and controlling disease injuries.

It was also found that the use of this agent in combination with leguminous bacteria or actinomycetes of the genus Streptomyces is highly effective for colonization of these useful microorganisms in soil. The present invention was accomplished on the basis of these findings.

Briefly, the present invention relates to a physiologically active agent for agricultural use which comprises, as active ingredient, a mixture of an N-acyl lactam compound represented by the general formula:

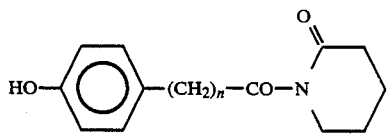

(wherein n is 1 or 2) and 2-piperidone. The present invention also relates to a physiologically active agent for agricultural use which comprises an N-acyl lactam compound, 2-piperidone and leguminous bacteria. The present invention further relates to a physiologically active agent for agricultural use which comprises an N-acyl lactam compound, 2-piperidone and actinomycetes of the genus Streptomyces.

The N-acyl lactam compounds of the present invention represented by the general formula:

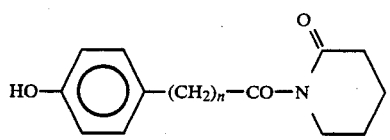

(wherein n is 1 or 2) may be prepared, for example, by the known methods disclosed in Japanese Patent Kokai No.246105 (1986), such as (1) reaction of lactam with an acid anhydride, and (2) reaction of lactam with an acid chloride.

The N-acyl lactam and 2-piperidone may be mixed together in the form of powder, or an intimate mixture can be obtained by dissolving the two compounds in a suitable solvent, mixing the two solutions thus obtained, and distilling off the solvent from the mixed solution.

There is no specific limitation upon the type of solvent used, and any solvent that is capable of dissolving the two compounds may be used for the purpose. But methanol, ethanol, acetone and ethyl acetate are generally employed. When catalytic reduction is adopted for the manufacture of the N-acyl lactam, 2-piperidone may be previously added in the reactor.

The mixing ratio of 2-piperidone to N-acyl lactam compound should preferably be in the range from 0.1 to 10 on a molar basis. If the molar ratio is less than 0.1, the effect of using 2-piperidone cannot be expected, while a mixing ratio exceeding 10 brings about no higher effect and is disadvantageous in terms of cost.

The physiologically active agents of the present invention are preferably applied in the form of a solution in terms of uniformity, but may also be used as a mixture with a suitable carrier, such as talc, cyclodextrin, dextrin, vermiculite, diatomaceous earth and silica powder.

The suitable amount to be used may vary with the type of plant, soil environment and intended purpose. Normally, an aqueous solution of 0.1 to 10 mg/l concentration is used in an amount of about one liter/m$^2$ for soil application, and an aqueous solution of 0.01 to 0.1 mg/l concentration is employed in an amount of 1 to 10 ton/10a for foliar application.

The agents of the present invention are preferably applied in the seedling stage (for example, in the potted state before planting, or within two weeks after planting), but may also be applied at any desired time.

Alternatively, the agents of the present invention may be previously applied to the soil prior to planting, or may be added, in hydroponics, to the water tank, to nutrients or to fertilizers used.

Detailed below is the physiologically active agent comprising an N-acyl lactam compound, 2-piperidone and leguminous bacteria of the genus Rhizobium.

As the leguminous bacteria of the genus Rhizobium to be used in the present invention, there may be exemplified, among others, *Rhizobium japonicum*, *R. leguminosarum* and *R. trifolii*.

The use of such a leguminous bacterium in combination with an N-acyl lactam compound and 2-piperidone is particularly effective in the cultivation of legumes.

Any leguminous bacteria which have been cultured by usual methods may be used for the purpose of the present invention.

These may be applied in the form of culture solution, as pellet obtained after centrifugal separation, or as a mixture with a suitable carrier as mentioned above (e.g., talc).

The physiologically active agent of the present invention containing a leguminous bacterium is most effective if applied around the root of each plant.

The suitable amount to be used may vary with the type of plant, soil environment and other factors. When used in the form of solution, it is preferable that a solution of 10$^6$ cell/ml concentration be applied in an amount of 1 liter/m$^2$.

The mixing ratio of 2-piperidone to N-acyl lactam compound should preferably be in the range mentioned above.

The agent is preferably applied to saplings.

Described below is the physiologically active agent comprising an N-acyl lactam compound, 2-piperidone and actinomycetes of the genus Streptomyces.

The physiologically active agent of the present invention using an actinomycetes of the genus Streptomyces in combination with an N-acyl lactam compound and 2-piperidone is particularly effective in promoting colonization of actinomycetes in soil.

As the actinomycetes of the genus Streptomyces to be used in the present invention, there may be exemplified, among others, *Streptomyces olivochromogenes*, *S. phaeochromogenes* and *S. griseolus*.

Any actinomycetes of the genus Streptomyces which have been cultured by usual methods may be used for the purpose of the present invention.

The application form and suitable amount to be used are the same as in the case with the agent containing leguminous bacteria described above.

Either soil or foliar application may be adopted, and there is no specific limitation on the time of application.

The physiologically active agents of the present invention show the following outstanding effects: (1) promoting the growth of plant roots; (2) proliferating leguminous bacteria of the genus Rhizobium and actinomycetes of the genus Streptomyces in soil, which are microorganisms useful for growing plants; and (3) suppressing the domination of bacteria of the genus Pseudomonas and pathogenic fungi imperfecti in soil, which are microorganisms responsible for the occurence of disease injuries.

Thus, use of the physiologically active agents of the present invention ensures normal growth of crops, bringing about higher yields especially in legumes.

In addition, the agent containing leguminous bacteria or actinomycetes of the genus Streptomyces facilitates colonization of the above-mentioned useful microorganisms in soil, which cannot be expected with conventional methods. The result is markedly increased crop yields (with leguminous bacteria), and prevention and alleviation of plant diseases (with actinomycetes of the genus Streptomyces).

The reason why such outstanding effects can be achieved by the agents of the present invention is not absolutely clear, but it may be assumed that the N-acyl lactam compound and 2-piperidone activate these useful microorganisms in soil, thus promoting their colonization.

These effects are a result of the favorable actions to soil microorganisms and to the growth of plant roots closely correlated to each other. In this respect, the physiologically active agents of the present invention are distinct from conventional plant growth regulators and agricultural chemicals.

Furthermore, the agents of the present invention are also excellent in terms of safety assurance, with no problem of environmental pollution and no harmful effect upon plants and animals. To prove this, a test was conducted to measure the physiochemical properties of the components in the agents of the present invention. Hydrolysis of the N-acyl lactam compounds showed that the half-life period at 35° C. is 30 minutes at pH 9.0, 8 hours at pH 7.0 and 18 hours at pH 4.0, and that the hydrolyzates are 2-piperidone and p-hydroxyphenylpropionic acid (a substance known to be a metabolite of tyrosine and found in the human blood and urine). 2-Piperidone is known to form, upon hydrolysis, 5-aminovaleric acid (an amino acid produced by enterobacteria through metabolism).

The invention is illustrated but not limited by the following Examples, in which: (1) % means weight % unless otherwise specified; (2) (molar ratio) for the physiologically active agents of the present invention is that of 2-piperidone to N-acyl lactam compound; (3) the N-acyl lactam compounds used are abbreviated as compounds No.1 and No.2, as shown in Table 1 below; and (4) the amount of compound No.1, compound No.2 and 2-piperidone, when used alone as comparative examples, is the same as that of the agent of the present invention.

TABLE 1

| Cpd. No | N-Acyl lactam compound |
|---|---|
| 1 | 1-[2-(4-Hydroxyphenyl)ethanoyl]-2-piperidone |
| 2 | 1-[2-(3-Hydroxyphenyl)propanoyl]-2-piperidone |

Incidentally all the microorganisms to be used in the present invention are already well known and readily available from the depositories listed below.

ATCC: American Type Culture Collection, Rockville, U.S.A.
IFO: Institute for Fermentation, Osaka, Japan
NCTC: National Collection of Type Culture, Central Public Health Laboratory, London, England
BUCSAV: Institute of Biology, Czechoslovak Academy of Sciences, Prague, CSSR
NCIB: National Collection of Industrial Bacteria, Torry Research Station, Aberdeen, Scotland
CBS: Centraalburean voor Schimmelcultures, Baarn, Netherland
RIA: The USSR Research Institute for Antibiotics, Moscow, USSR Hence, each of the microorganisms shown in the following Examples will be given its deposit number.

EXAMPLE 1

Physiologically active agents of the present invention (molar ratio: 1) were dissolved in ethyl acetate, giving test solutions of definite concentrations as shown in Table 2.

Each of the test solutions (2 ml) was added to a piece of filter paper (70 mmφ) placed in a petri dish, the solvent was distilled off under reduced pressure, 2 ml of sterile water was added, and seeds of Brassica rapa L. (25 pieces) were sown and held at 25° C. in the dark.

For control, the same procedure as above was repeated except that ethyl acetate alone was used.

The length of grown root was measured after 48 hours, and the root growing rate was calculated from the difference from the data of control. The result is summarized in Table 2.

TABLE 2

| Test Samples | Root Growing Rate (%) | | | |
|---|---|---|---|---|
| | 0.001 mg/l | 0.01 mg/l | 0.1 mg/l | 1 mg/l |
| Agents of this invention: | | | | |
| Agent No. 1 | +45 | +25 | +20 | +10 |
| Agent No. 2 | +40 | +35 | +30 | +24 |
| Comparative examples: | | | | |
| 2-Piperidone | −1 | +2 | +3 | −2 |
| Compound No. 1 | +4 | +30 | +20 | +15 |
| Compound No. 2 | −3 | +3 | +10 | +9 |

(Note) The root growing rate was calculated from the following equation:

$$\text{Root growing rate (\%)} = \frac{(\text{Av. measurements of test zone}) - (\text{Av. measurements of control zone})}{(\text{Av. measurements of control zone})} \times 100$$

Agent No. 1: Compound No. 1 + 2-piperidone
Agent No. 2: Compound No. 2 + 2-piperidone

EXAMPLE 2

Twenty-five pieces of germinated seeds of rice plant ("Nippon-bare") were set on 2% agar placed in a petri dish, with each coleoptile facing upward, and grown in the dark at 25° C. for two days while properly sprinkling water.

A test solution in 50% acetone (1 μl) of the concentration shown in Table 3 was added between the first leaves of grown seedlings by means of a microsyringe, and cultivation was further continued.

For control, the same procedure as above was repeated except that 50% acetone alone was used.

The results obtained are summarized in Table 3.

TABLE 3

| Molar Ratio | Concn. (mg/l) | Plant Height after: | | | | Root Growing Rate (%) |
|---|---|---|---|---|---|---|
| | | 1 day | 2 days | 5 days | 7 days | |
| Agents of this invention: | | | | | | |
| 0.1 | $10^{-5}$ | 93 | 159 | 461 | 665 | +4 |
| | $10^{-4}$ | 97 | 176 | 465 | 703 | +8 |
| | $10^{-3}$ | 101 | 177 | 472 | 700 | −6 |
| 2 | $10^{-5}$ | 94 | 167 | 419 | 708 | −2 |
| | $10^{-4}$ | 88 | 158 | 439 | 731 | +18 |
| | $10^{-3}$ | 104 | 190 | 469 | 757 | +21 |
| 10 | $10^{-5}$ | 95 | 161 | 394 | 687 | −4 |
| | $10^{-4}$ | 101 | 167 | 412 | 686 | +6 |
| | $10^{-3}$ | 97 | 173 | 397 | 672 | +11 |
| Comparative examples: | | | | | | |
| Compound No. 2 | $10^{-5}$ | 100 | 167 | 425 | 685 | −2 |
| | $10^{-4}$ | 101 | 172 | 435 | 695 | −1 |
| | $10^{-3}$ | 101 | 175 | 456 | 693 | +5 |
| 2-Piperidone | $10^{-5}$ | 95 | 171 | 413 | 685 | −3 |
| | $10^{-4}$ | 97 | 176 | 418 | 684 | −3 |
| | $10^{-3}$ | 101 | 177 | 425 | 698 | +4 |
| Control | — | 100 | 174 | 414 | 687 | — |

(Notes)
The root growing rate was calculated in the same way as in Example 1.
The plant height is expressed with the value of control group after 24 hours taken as 100.

EXAMPLE 3

Physiologically active agents of the present invention (molar ratio: 1) were each dissolved in ethyl acetate in a conical flask, and the solvent was distilled off under reduced pressure, giving test flasks.

Separately, each of the strains shown in Table 4 was inoculated to 50 ml of a liquid medium containing 2% malt extract, static culture was continued at 25° C. for four days, and the mycelium developed was collected and dispersed in sterile water, giving a microbial test solution.

A culture medium of the composition shown in Table 5 (50 ml each) was distributed in the test flasks prepared above (100-ml capacity, each containing 5 mg test sample), each flask was treated in an ultrasonic wave tank to completely disperse the test sample, 1 ml of a microbial test solution obtained above was inoculated, and static culture was continued at 25° C. for ten days. The weight of dry microbial cells was then measured, and the rate of change in weight of microbial cells was calculated. For control, the same procedure as above was repeated except that ethyl acetate alone was used.

The results are summarized in Table 6.

TABLE 4

| No. | Strain |
|---|---|
| (1) | *Alternaria solani* IFO-7516 |
| (2) | *Botrytis byssoidea* IFO-9431 |
| (3) | *Cladosporium colocasiae* IFO-9345 (ATCC-38014) |
| (4) | *Fusarium oxysporum* IFO-7152 |
| (5) | *Gibberella fujikuroi* IFO-30336 |
| (6) | *Stemphylium lycopersici* IFO-6679 |
| (7) | *Verticillium albo-atrum* IFO-9470 |

TABLE 5

| Glucose | 1.0 g |
|---|---|
| $(NH_4)_2SO_4$ | 0.5 g |
| $K_2HPO_4$ | 0.1 g |
| $KH_2PO_4$ | 0.25 g |
| B-Solts* | 1 ml |
| Distilled water | 100 ml |
| pH | 6.0 |
| $MgSO_4\ 7H_2O$ | 10 g |
| NaCl | 0.5 g |
| $FeSO_4\ 7H_2O$ | 0.5 g |
| $MgSO_4\ 4H_2O$ | 0.5 g |
| Distilled water | 250 ml |

*B-Solts

TABLE 6

| No. of strain tested | Rate of Change in Weight of Microbial Cells (%)* | | | | |
|---|---|---|---|---|---|
| | Agents of this invention | | Comparative examples | | |
| | Agent No. 1 | Agent No. 2 | Cpd. No. 1 | Cpd. No. 2 | 2-Piperidone |
| (1) | −43 | −41 | −30 | −33 | −7 |
| (2) | −25 | −15 | −10 | +364 | +21 |
| (3) | −7 | +3 | −5 | +11 | −14 |
| (4) | −34 | −46 | −25 | 0 | −4 |
| (5) | −23 | −39 | −15 | −11 | −10 |
| (6) | −58 | −30 | −52 | −32 | −5 |
| (7) | −20 | −27 | −23 | −13 | −7 |

*The rate of change in weight of microbial cells was calculated from the following equation:
Rate of change in weight of microbial cells (%) =

$$\frac{\text{Dry weight in test zone(mg)} - \text{Dry weight in control zone(mg)}}{\text{Dry weight in control zone(mg)}} \times 100$$

It is apparent from the results shown in Table 6 that the physilogically active agents of the present invention markedly control the propagation of the fungi.

EXAMPLE 4

Physiologically active agents of the present invention (molar ratio: 0.2) were dissolved in acetone to a concentration of 10 mg/l, a disk for testing antibiotics (8 mmφ) was dipped in each of the solutions prepared above, and the solvent was removed by evaporation, thus giving test disks.

An agar medium containing 2% malt extract was put in a petri dish, the water on the surface was wiped off, a test disk prepared above was set on the medium, and 0.05 ml of a microbial solution prepared from strain No.(4) in Table 4 in the same way as in Example 3 was inoculated.

Static culture was continued at 25° C. for ten days, the microbial growth area on the surface was measured from the fourth day (on which growth of hyphae was observed) and thereafter, and the ratio of growth area was calculated.

For control, the same procedure as above was repeated except that acetone alone was used.

The results obtained are summarized in Table 7.

TABLE 7

| Test Sample | Ratio of Growth Area* for Strain No. (4) | | | | |
|---|---|---|---|---|---|
| | 4th day | 5th day | 6th day | 7th day | 8th day |
| Agents of this invention: | | | | | |
| Agent No. 1 | 1.0 | 1.7 | 0.8 | 0.4 | 0.2 |
| Agent No. 2 | 0.9 | 1.4 | 0.7 | 0.3 | 0.2 |
| Comparative examples: | | | | | |
| Compound No. 1 | 1.2 | 0.7 | 0.7 | 0.6 | 0.6 |
| Compound No. 2 | 0.8 | 0.7 | 0.5 | 0.5 | 0.5 |
| 2-Piperidone | 1.3 | 1.2 | 1.2 | 1.0 | 0.9 |

The ratio of microbial growth area* was calculated from the following equation:

$$\text{Rate of microbial growth area} = \frac{\text{Growth area in test zone (cm}^2\text{)}}{\text{Growth area in control zone (cm}^2\text{)}}$$

It is apparent from the results shown in Table 7 that the physiologically active agents of the present invention are not fungicidal agents; the fungi propagate in the initial stage, a maximum is reached on the 5th day, and then gradual decay occurs.

EXAMPLE 5

Each of the strains listed in Table 8 was cultured at 30° C. using a slant medium of the composition shown in Table 9. Immediately after confirming grown cells on the slant surface, the cells were stored at 4° C. as master culture for the succeeding test.

In a 100-ml conical flask, was placed 0.5 ml of an ethyl acetate solution (1000 mg/l) of the physiologically active agents of the present invention (molar ratio: 0.5), the solvent was distilled off, and 50 ml of a bouillon liquid medium was added.

One loop of the master culture prepared above was inoculated to 10 ml of the bouillon liquid medium and evenly dispersed, and 0.5 ml of this dispersion was inoculated to the conical flask.

For control, the same procedure as above was repeated except that ethyl acetate alone was used.

Cultivation was continued at 30° C. for 48 hours, and the number of grown cells was counted by means of a Petroff-Housser counting chamber. The results are summarized in Table 10.

TABLE 8

| No. | Strain |
|---|---|
| (11) | *Pseudomonas aeruginosa* IFO-3080 |
| (12) | *Pseudomonas aureofaciens* IFO-3521 (ATCC-13985; NCIB-9030) |
| (13) | *Pseudomonas putida* IFO-3738 (ATCC-8209; NCIB-8296; BUCSAV-290) |

TABLE 8-continued

| No. | Strain |
|---|---|
| (14) | *Pseudomonas diminuta* IFO-12697 (ATCC-11568; NCTC-8545) |

TABLE 9

| | |
|---|---|
| Potato extract* | 200 g |
| Expressed yeast | 30 g |
| Liver extract** | 25 g |
| Meat extract | 5 g |
| Thioglycolic acid medium | 10 g |
| Glucose | 5 g |
| Glycerol | 15 g |
| Agar | 15 g |
| Distilled water | (to make up 1 liter) |
| pH | 7.0 |

(Notes)
*Potato (100 g) was peeled, cut into cubes of about 1 cm square, boiled in 500 ml of tap water for 30 minutes, cooled and freed from solid matters.
**Liver (50 g) was sliced, boiled in 150 ml of tap water for 30 minutes, cooled and freed from solid matters.

TABLE 10

| Sample | Strain No. Number of cells per milliliter | | | |
|---|---|---|---|---|
| | (11) | (12) | (13) | (14) |
| Agents of this invention: | | | | |
| Agent No.1 | $1.3 \times 10^8$ | $1.5 \times 10^8$ | $1.0 \times 10^8$ | $1.2 \times 10^8$ |
| Agent No.2 | $2.7 \times 10^8$ | $1.6 \times 10^8$ | $1.7 \times 10^8$ | $2.3 \times 10^8$ |
| Comparative examples: | | | | |
| Compound No. 1 | $6.8 \times 10^9$ | $2.1 \times 10^9$ | $3.0 \times 10^9$ | $2.5 \times 10^9$ |
| Compound No. 2 | $6.8 \times 10^9$ | $7.2 \times 10^9$ | $7.3 \times 10^9$ | $9.1 \times 10^9$ |
| 2-Piperidone | $4.3 \times 10^{10}$ | $8.1 \times 10^{10}$ | $5.0 \times 10^{10}$ | $1.8 \times 10^{10}$ |
| None | $3.5 \times 10^{10}$ | $7.3 \times 10^{10}$ | $5.7 \times 10^{10}$ | $4.3 \times 10^{10}$ |

As is apparent from Table 10, the physiologically active agents of the present invention are effective in controlling the propagation of the bacteria.

EXAMPLE 6

Physiologically active agents of the present invention (molar ratio: 0.1, 1 and 10) were each added to an agar medium of the composition shown in Table 12 to a concentration of 0.1 mg/l. One loop of microorganism shown in Table 11 was suspended in 10 ml of sterile water, 0.1 ml of the suspension thus prepared was inoculated to the above agar medium, and plate culture was continued at 25° C.

The total number of grown cells was counted and their shape observed on the seventh day.

The results are summarized in Table 13.

TABLE 11

| No. | Strain |
|---|---|
| (I) | *Rhizobium trifolii* IFO-13337 |
| (II) | *Rhizobium japonicum* IFO-13338 |
| (III) | *Rhizobium leguminosarum* IFO-14168 |

TABLE 12

| | |
|---|---|
| Yeast extract | 1 g/l |
| Mannitol | 10 g/l |
| Soil extract* | 200 ml/l |
| Agar | 15 g/l |
| pH | 7.2 |

*Soil extract: Soil (1 Kg) was extracted with 500 ml water at 121° C. for 30 minutes, the mixture was allowed to stand overnight, and the filtrate was diluted to 1000 ml.

TABLE 13

| No. of strain tested | Total Number and Shape of Cells | | | | | | |
|---|---|---|---|---|---|---|---|
| | Comp. Examples Untreated | Agents of this invention | | | | | |
| | | No. 1 (0.1) | No. 1 (1) | No. 1 (10) | No. 2 (0.1) | No. 2 (1) | No. 2 (10) |
| (I) | 1 | 2 | 1.5 | 1.2 | 1.5 | 2 | 1 |
| | R | B | B | B | B | B | B |
| (II) | 1 | 3 | 3 | 2.5 | 1.5 | 3 | 1.5 |
| | R | B | B | B | B | B | B |
| (III) | 1 | 2.5 | 2.5 | 1 | 1 | 3 | 1.5 |
| | R | B | B | B | B | B | B |

(Notes)
The total number of cells are expressed as the factor to the value of untreated samples.
The shape of cells is shown in the lower column. R: Rod-form; B: Bacteroid
Values in ( ) show molar ratio.

As can be seen from Table 13, use of the active agents of the present invention promotes the propagation of leguminous bacteria by a factor of about 1.5 to 3 and also makes the cells larger into the form of bacteroid.

EXAMPLE 7

Wagner pots (1/5000 are) were filled with a mixture of soil and compost (1:1), and fertilizers were applied so that the N-$P_2O_5$-$K_2O$ ratio will be 0.5-0.5-0.5/pot.

To each of the pots thus prepared, were sown five pieces each of Glicine max Merr. at three sites (a total of 15 pieces).

After ten days, the grown seedlings were thinned out to leave three pieces of uniform height at each site.

Fourteen days after sowing, 20 ml of an alcoholic solution of test sample listed in Table 14 was evenly applied around the roots, and the plants were grown while properly sprinkling water and controlling insects and diseases.

Seventy-four days after sowing, the number and weight of root nodules were measured, the result of which is shown in Table 15.

TABLE 14

| Test No. | Sample Solutions Prepared | |
|---|---|---|
| | Legum. bacteria* | Additives (10 mg/l) |
| 1 | — | — |
| 2 | — | 2-Piperidone |
| 3 | — | Compound No. 1 |
| 4 | — | Agent No. 1 of this invention (mole ratio:1) |
| 5 | — | Agent No. 2 of this invention (mole ratio:1) |
| 6 | II | — |
| 7 | II | 2-Piperidone |
| 8 | II | Compound No. 1 |
| 9 | II | Agent No. 1 of this invention (mole ratio:1) |
| 10 | II | Agent No. 2 of this invention (mole ratio:1) |

*Leguminous bacteria II: Cells obtained in Example 6 by culture of strain (II) at 25° C. for 10 days were suspended in sterile water so as to give an absorbance of 0.3 at 660 nm.

TABLE 15

| Test No. | Weight of Nodules (g) | Number of Nodules |
|---|---|---|
| Agents of this invention: | | |
| 4 | 30.7 | 656 |
| 5 | 35.5 | 719 |
| Comparative examples: | | |
| 1 | 22.9 | 451 |
| 2 | 23.1 | 436 |
| 3 | 23.3 | 466 |
| Agents of this invention: | | |
| 9 | 33.8 | 729 |
| 10 | 29.7 | 609 |

TABLE 15-continued

| Test No. | Weight of Nodules (g) | Number of Nodules |
|---|---|---|
| Comparative examples: | | |
| 6 | 30.4 | 541 |
| 7 | 23.8 | 488 |
| 8 | 28.5 | 503 |

As is apparent from Table 15, both the weight of root nodules and the number of leguminous bacteria are increased by the use of the physiologically active agents of the present invention.

EXAMPLE 8

This Example is to illustrate that use of the physiologically active agents of the present invention remarkably promotes the propagation of actinomycetes of the genus Streptomyces.

One loop of a strain listed in Table 16 was inoculated to a slant medium of the composition shown in Table 17, and incubated at 30° C.

One loop of the grown cells thus obtained was then inoculated to a liquid medium of the composition shown in Table 17, and shake culture was continued at 30° C. for 72 hours to give a master culture.

Separately, ethanolic solutions of physiologically active agents of the present invention (molar ratio: 0.5) were diluted with sterile water to give solutions of $10^{-1}$, 1.0 and 10 mg/l concentrations, and each of the solutions thus prepared (2 ml) was placed in a petri dish.

To this petri dish, was added 18 ml of agar medium of the composition shown in Table 17 to which 0.1 ml of the master culture had been inoculated, and plate culture was continued at 30° C.

For control, the same procedure as above was repeated except that the same volume of ethanol was used.

The number of colonies developed was counted on the seventh day, and the results obtained are summarized in Table 18.

Similar tests were conducted with the strains listed in Table 19 using the agent No. 1 of the present invention. The number of colonies developed was about 1.5 to 2.2 times as much compared with the case using no active agent of the present invention.

TABLE 16

| No. | Strain | |
|---|---|---|
| (i) | Streptomyces canus | IFO-12752 (ATCC-12237 & 19737; CBS-475.68; RIA-1017) |
| (ii) | Streptomyces fradiae | IFO-12773 (ATCC-10745 & 19760; CBS-498.69; RIA-1040) |

TABLE 17

| Yeast extract | 4 g |
|---|---|
| Malt extract | 10 g |
| Glucose | 4 g |
| Distilled water | 1 L |
| pH | 7.3 |
| (Agar | 20 g) |

TABLE 18

| Strain | Test Sample | Number of colonies/dish | | |
|---|---|---|---|---|
| | | $10^{-2}$ mg/l | $10^{-1}$ mg/l | 1 mg/l |
| (i) | Agents of this invention: | | | |
| | Agent No. 1 | 301 | 418 | 345 |
| | Agent No. 2 | 325 | 435 | 332 |

TABLE 18-continued

| Strain | Test Sample | Number of colonies/dish | | |
|---|---|---|---|---|
| | | $10^{-2}$ mg/l | $10^{-1}$ mg/l | 1 mg/l |
| | Comparative examples: | | | |
| | None | | 219 | |
| | 2-Piperidone | 223 | 231 | 238 |
| | Compound No. 1 | 234 | 382 | 280 |
| | Compound No. 2 | 249 | 351 | 283 |
| (ii) | Agents of this invention: | | | |
| | Agent No. 1 | 429 | 567 | 490 |
| | Agent No. 1 | 475 | 501 | 562 |
| | Comparative examples: | | | |
| | None | | 292 | |
| | 2-Piperidone | 290 | 295 | 310 |
| | Compound No. 1 | 314 | 431 | 383 |
| | Compound No. 2 | 306 | 381 | 351 |

TABLE 19

| No. | Strain |
|---|---|
| A | *Streptomyces olivochromogenes* IFO-3404 |
| B | *Streptomyces phaeochromogenes* IFO-12898 |
| C | *Streptomyces griseolus* IFO-3402 |
| D | *Streptomyces lipmanii* IFO-12791 |
| E | *Streptomyces kurssanovii* IFO-13192 |
| F | *Streptomyces fradiae* IFO-12773 |
| G | *Streptomyces californicus* IFO-12750 |
| H | *Streptomyces griseus subspecies griseus* IFO-12875 |
| I | *Streptomyces olivaceus* IFO-12805 |
| J | *Streptomyces alboflavus* IFO-13196 |
| K | *Streptomyces griseosporeus* IFO-13458 |

EXAMPLE 9

An ethanolic solution of physiologically active agent No. 1 of the present invention (molar ratio: 1.5) was diluted with water to give a test solution of 10 mg/l concentration.

Separately, a wild type strain of the genus Streptomyces collected in a field was subjected to shake culture for four days using a liquid medium of the composition shown in Table 12.

To one liter of this culture solution, was added 100 ml of the test solution prepared above.

One part of this active agent containing microbial cells was then mixed with ten parts of diatomaceous earth, giving a microbial sample for field test.

This microbial sample was applied to 50 plants of cucumber (*Cucumis sativus*), which had been grown for 50 days in a field and suffering from injuries by Botrytis cinerea, on the lesion area in aerial part.

For control, diatomaceous earth alone was applied to the lesion area of other 50 plants.

The progress of disease injuries was observed till the time of harvesting, and the number of plants capable of harvesting was counted in the final stage.

The result is shown in Table 20.

TABLE 20

| Test Sample | Plants Capable of Harvesting (%) |
|---|---|
| Diatomaceous earth | 4 |
| None | 16 |
| 2-Piperidone | 22 |
| Compound No. 2 | 30 |
| Agent No. 2 | 82 |

EXAMPLE 10

The test solution prepared in Example 9 was diluted with water to a concentration of 0.2 g/l, and this dilution was applied to 100 plants of tomato (*Lycopersicon eculentum* Mill.) grown in a field for ten days after plantation (soil application in an amount of 1 l/m²).

The condition of disease injuries was investigated on the 60th day after application, the result of which is shown in Table 21. The incidence of plant diseases was determined by judging from the presence or absence of lesion areas of aerial part, the dwarfing degree of leaves and stems, and the condition of fructification.

Separately, soil samples were collected from the test and control zones, and the distribution of autochthonous microorganisms in the rhizosphere was measured according to the procedure described below.

The soil samples (50 to 100 g) were taken into a sterile bag from areas 30 cm deep and 30 cm apart from the root of each plant, the collected samples were mixed well in the bag, and 2 g of this mixture was placed in a 50-ml spiry tube.

Sterile water (10 to 15 ml) was then added, the mixture was shaken in a flush mixer for one minute and allowed to stand for one minute, and the supernatant was removed by decantation. This operation was repeated to wash the soil with a total of 100 ml sterile water. The above operations were repeated ten times.

The same procedure as above was repeated once again by using a total of 200 ml sterile water. Into the washed soil thus obtained, were put several pieces of sterile filter paper to absorb excess water, giving a sample soil for analysis of microrganisms.

This sample soil was spread on 20 petri dishes, 10 ml each of an agar medium (containing 2% agar and 2% malt extract) was poured to ten of the twenty dishes, 10 ml each of an agar medium of the composition shown in Table 12 was poured to the remaining ten dishes, and plate culture was continued at 25° C. for 14 days.

The colonies developed in the latter ten dishes were isolated, Gram-stained, and observed under an microscope to count bacteria and yeasts involved. Colonies of the species other than the bacteria and yeasts were inoculated to ISP medium, species belonging to the genus Streptomyces were identified from the morphological features and cell wall composition, and their distribution rate was determined (visible frequency).

From the former ten dishes, hyphae were cut out and incubated to form conidiospores, and genus identification was made based on morphological observation to determine the distribution rate (visible frequency).

These results are summarized in Table 22.

TABLE 21

| Test Sample | Plant Disease Incidence (%) |
|---|---|
| Agent of this invention: | |
| Agent No. 2 | 5.1 |
| Comparative examples: | |
| None | 18.5 |
| 2-Piperidone | 19.6 |
| Compound No. 2 | 15.3 |

TABLE 22

| Types of Microorganisms Living in Rhizosphere | Number of Miroorganisms (colony/g-soil) | |
|---|---|---|
| | Control zone | Test zone |
| Total number of cells | 3307 | 3785 |
| Total number of fungi | 479 | 139 |
| Number of streptomycetes | 591 | 1535 |
| Distribution rate of streptomycetes (%) | 17.9 | 40.6 |

EXAMPLE 11

A pot test was conducted to examine the effect of the physiologically active agent of the present invention upon the crop of soybeans.

The conditions of soybean cultivation and application of the agent are as shown below.

Cultivation of Soybean

Base manure: $N$-$P_2O_5$-$K_2O$ = 1.5-1.5-1.5 (g/pot)

Time of sowing: Jul., 1986.
Time of harvesting: Nov., 1986.
Application of Agent
(1) Type of agent: Physiologically active agent No. 1 (molar ratio: 1)
(2) Concentration and amount applied: 1 mg/l; 1 l/m²
(3) Application time: 15 days after sowing
(4) Potting condition: three-row, 1/2000 are pots; four plants per pot The result of harvesting is shown in Table 23.

TABLE 23

| Test Sample | Weight of Polished Beans (g) | Number of Polished Beans |
|---|---|---|
| Agent of this invention: | | |
| Agent No.1 | 86.2 | 268 |
| Comparative examples: | | |
| None | 66.3 | 203 |
| 2-Piperidone | 67.1 | 199 |
| Compound No. 1 | 69.6 | 228 |

EXAMPLE 12

A field test was conducted in Kasai City (Hyogo Prefecture, Japan) to examine the effect of the physiologically active agent of the present invention upon the crop of potatoes (*Solanum tuberosam* L.).

The conditions of potato cultivation and application of the agent are as shown below.

Cultivation of Potatoes
Base manure: $N$-$P_2O_5$-$K_2O$ = 11-14-16 (Kg/10a).
Time of sowing: Aug., 1987.
Time of harvesting: Dec., 1987.
Application of agent
(1) Type of agent: Physiologically active agent No. 2 (molar ratio: 1)
(2) Concentration and amount applied: 1 mg/l; 1 l/m²
(3) Application time: 20 days after sowing
(4) Test plants: 30 plants of potato Quality and yield of the harvested potatoes are summarized in Tables 24 and 25, in which the quality is evaluated in terms of the severity of diseases observed (scabs and powdery scabs).

TABLE 24

| Test Sample | Weight of Leaved Stems (Kg,a) | Weight of Roots (Kg/a) | Number of Roots (/a) |
|---|---|---|---|
| Agent of this invention: | | | |
| Agent No. 2 | 213 | 529 | 4033 |
| Comparative examples: | | | |
| None | 193 | 461 | 3965 |
| 2-Piperidone | 208 | 457 | 4020 |
| Compound No. 2 | 186 | 473 | 4083 |

TABLE 25

| Test Sample | Number of Potatoes Tested | Number of Potatoes Suffering Scabs and the Like of Different Severities | | | |
|---|---|---|---|---|---|
| | | Serious | Considerable | Slight | No scab |
| Agent of this invention: | | | | | |
| Compound No. 2 | 200 | 6 | 18 | 87 | 89 |
| Comparative examples: | | | | | |
| None | 200 | 38 | 84 | 54 | 24 |
| 2-Piperidone | 200 | 42 | 56 | 68 | 34 |
| Compound No. 2 | 200 | 21 | 43 | 108 | 28 |

EXAMPLE 13

A field test was conducted in Himeji City (Hyogo Prefecture, Japan) to examine the effect of the physiologically active agent of the present invention upon the crop of green soybeans (*Glicine max* Merr.).

The conditions for cultivation and application of the agent are as shown below.

Cultivation
Base manure: $N$-$P_2O_5$-$K_2O$ = 6.4-5.6-5.6 (70–80 Kg/10a).
Time of sowing: Apr., 1987.
Time of harvesting: Jul., 1987.
Application of Agent
(1) Type of agent: Physiologically active agent No. 2 (molar ratio: 1)
(2) Concentration and amount applied: 1 mg/l; 1 l/m²
(3) Application time: 17 days after sowing.
(4) Test plants: 30 plants of green soybean.

The yield of beans was measured and the averaged data per plant calculated. The results are summarized in Table 26.

Separately, distribution of the autochthonous microorganisms in the rhizosphere was measured by microbial analysis in the same way as described in Example 10 to examine the effect of the physiologically active agent of the present invention upon microorganisms in soil. The genus of each microorganism was identified according to the method described in "Bergey's Manual of Determinative Bacteriology (8th edition)", "Methodology for Identifying Actinomycetes (edited by Japan Actinomycetes Research Association)", and "Pictorial Book of Fungi (written by S. Udagawa and K. Tsubaki). The results are shown in Table 27.

TABLE 26

| | Test Sample | | | |
|---|---|---|---|---|
| | Agent of This Invention | Comparative Examples | | |
| | | Cpd. No. 2 | None | 2-Piperidone |
| Total fresh weight (g) | 360.2 | 325.8 | 314.8 | 318.1 |
| Root weight (g) | 32.5 | 21.3 | 17.6 | 17.8 |
| Fresh weight of aerial part (g) | 327.7 | 304.5 | 297.2 | 300.3 |
| Plant length (cm) | 33.9 | 25.0 | 25.2 | 25.6 |
| Stem diameter (cm) | 11.5 | 11.5 | 11.4 | 11.4 |
| Total pod weight (g) | 162.5 | 150.2 | 149.1 | 150.1 |
| Total number of pods | 58.9 | 50.7 | 50.8 | 50.6 |
| Weight of pods with | 68.8 | 53.1 | 53.0 | 52.1 |

TABLE 26-continued

| | Test Sample | | | |
|---|---|---|---|---|
| | Agent of This Invention | Comparative Examples | | |
| | | Cpd. No. 2 | None | 2-Piperidone |
| 3 or more grains (g) Number of pods with 3 or more grains | 20.0 | 12.5 | 12.2 | 11.7 |

TABLE 27

| Types of Autochthonous Microorganisms in the Rhizosphere | Number of Microorganisms 14 Days after Application (isolation frequency/g-soil) | |
|---|---|---|
| | This invention | Untreated |
| Absidia sp. | 2 | — |
| Arthrinium sp. | — | — |
| Aspergillus sp. | 2 | — |
| Aureobasidium sp. | 2 | — |
| Bipolaris sp. | — | — |
| Botrytis sp. | 20 | 44 |
| Candida sp. | 2 | — |
| Chaetomium sp. | — | — |
| Chrysosporium sp. | 20 | — |
| Cladosporium sp. | 16 | — |
| Curvularia sp. | — | — |
| Fusarium sp. | 138 | 134 |
| Geotrichum sp. | 2 | — |
| Monilia sp. | — | — |
| Mucor sp. | 8 | 16 |
| Paecilomyces sp. | 10 | — |
| Penicillium sp. | 10 | — |
| Phoma sp. | 2 | — |
| Rhizoctonia sp. | 2 | — |
| Rhizopus sp. | 2 | — |
| Sepedonium sp. | 2 | — |
| Torula sp. | 10 | — |
| Trichoderma sp. | 18 | — |
| Verticillium sp. | — | — |
| Total number of fungi* | 266 | 194 |
| Number of Streptomyces sp. | 2134 | 328 |
| Total number of cells | 5248 | 3044 |
| Distribution rate of fungi (%)** | 5.1 | 6.4 |
| Distribution rate of Streptomyces sp. (%)*** | 40.7 | 10.8 |

(Notes)
Total number of fungi*: Including unidentified fungi.
Distribution rate of fungi(%)**: Ratio to total number of cells
Distribution of Streptomyces sp. (%)***: Ditto

EXAMPLE 14

The effect of the physiologically active agent of the present invention to prevent disease injuries in the cultivation of tomato (*Lycopersicon eculentum* Mill.) was tested at three fields in Himeji and Tatsuno Cities (Hyogo Prefecture, Japan).

To seedlings planted in Jul., was applied the agent prepared in the same way as in Example 13 under the same conditions 10 days after plantation, and tolerance of the treated plants to diseases was examined. In each of the fields, test and control zones of equal area were set and about 1500 plants (on average) were tested.

Sixty days after plantation, each plant was checked, those in which symptoms of bacterial wilt, Fusarium wilt or bacterial soft rot was observed in more than about 30% area were regarded as injured plants, and the incidence of disease injuries was calculated (as percentage based on the total number of plants). The results are summarized in Table 28.

TABLE 28

| | Test Sample Incidence of Disease Injuries (%) | | | |
|---|---|---|---|---|
| | Agent of this invention | Comparative examples | | |
| Field | | Compound No. 2 | 2-Piperidone | None |
| A | 14.8 | 24.0 | 25.6 | 24.5 |
| B | 0 | 7.5 | 7.1 | 6.5 |
| C | 1.2 | 45.1 | 53.5 | 53.1 |

What we claim is:

1. A soil amending agent comprising a mixture of 2-piperidone and an N-acyllactam compound represented by the formula:

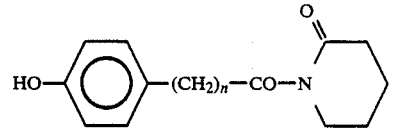

wherein n is 1 or 2,
and wherein the molar ratio of 2-piperidone to N-acyllactam compound is in the range from 0.1:1 to 10:1.

2. A soil amending agent as defined in claim 1 which further contains leguminous bacteria of the genus Rhizobium.

3. A soil amending agent as defined in claim 1 which further contains actinomyces of the genus Streptomyces.

* * * * *